US006489543B1

(12) United States Patent
Sernyk

(10) Patent No.: US 6,489,543 B1
(45) Date of Patent: Dec. 3, 2002

(54) **SPRING CANOLA (*BRASSICA NAPUS*) VARIETY SVO95-08**

(75) Inventor: Larry Sernyk, Lebanon, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 09/642,992

(22) Filed: Aug. 21, 2000

(51) Int. Cl.$^7$ .............................. A01H 4/00; A01H 1/00; A01H 5/00; A01H 5/10
(52) U.S. Cl. ........................ 800/306; 800/268; 800/264; 435/430
(58) Field of Search .................................. 800/306, 268, 800/264; 435/430

(56) References Cited

U.S. PATENT DOCUMENTS 6,414,223 B1 * 7/2002 Kodali et al. ................ 435/468

OTHER PUBLICATIONS

Global; PVP No. 8500114. Filed 4/85,.issued 2/87 Germplasm Resources Information Network—(GRIN). National Germplasm Resources Laboratory, Beltsville, MD. (Version Date Oct. 4, 2001) http://www.ars–grin.gov/.*

Anonymous. 1990.Canola (Brassica napus). Plant Varieties J. 3(3):8–10.*

Adang, M. J., K. F. Idler, and T., A. Rocheleau (1987) "Structural and antigenic relationships among three insecticidal crystal proteins of *Bacillus thuringiensis subsp.* kurstaki," Biotechnology in Invertebrate Pathology and Cell Culture. Maramorosch, K. (Ed.) Academic Press, pp. 85–99.

Anandarajah K. and B.D. McKersie (1990) "Manipulating the desication tolerance and vigor of dry somaticembryos of *Medicago sativa* L. with sucrose, heat shock and abcisic acid," Plant Cell Rep. 9: 451–455.

Christie, W. W. (1982) "A simple procedure for rapid transmethylation of glycerolipids and cholesteryl esters," *J. Lipid. Res.* 23: 1072–1075.

Chuong, P. V. and W.D. Beversdorf(1985) "High frequency embryogenesis through isolated microspore culture in *Brassica napus* L. and *B.carinata* Braun," Plant Sci. 39: 219–226.

Finkelstein, R. R. and M.L. Crouch (1987) "Hormonal and osmotic effects on developmental potential of maturing rapeseed,"Hort Sci. 22: 797–800.

Finkelstein, R. R. and C. Somerville (1989) "Abcisic acid or high osmoticum promote accumulation of long–chain fatty acids in developing embryos of *Brassica napus*," Plant Sci. 61: 213–217.

Frohman, M.A. (1988) "Rapid production of full–length cDNAs from rare transcripts: Amplification using a single gene–specific oligonucleotide primer," *Proc. Natl. Acad. Sci. (USA)* 85:8998–9002.

Gamborg, O.L., R.A. Miller, and K. Ojima (1986) "Nutrient requirements of suspension cultures of soybean root cells," *Expt. Cell Res.* 50:151–158.

Kott, L. S., L.R. Erickson, and W.D. Beversdorf (1990) "The role of biotechnology in canola/rapeseed research," In: Canola and Rapeseed: Production, Nutrition and Processing Technology. F. Shahidi ed. Van Nostrand Reinhold, New York. pp. 47–78.

Lichter, R. (1981) "Another culture of *Brassica napus* in a liquid culture medium," *Z. Pflanzenphysiol.* 103: 229–237.

Lichter, R. (1982) "Induction of Haploid plants from isolated pollen of *Brassica napus*," *Z. Pflanzenphysiol.* 105: 427–434.

Mathias, R. (1988) "An inproved in vitro culture procedure for embryoids derived from isolated microspores of rape (*Brassica napus* L.)," Plant Breeding 100: 320.

Murashige, T. and F. Skoog (1962) "A revised medium for rapid growth and bioassays with tobacco tissue cultures," *Physiol. Plant.* 15:473–497.

Nitsch, C. and J.P. Nitsch (1967) "The induction of flowering in vitro in sterm segments of L *Plumbago indica*," Planta 72: 355–370.

Reiss, B., R. Sprengel, H. Will, and H. Schaller (1984) "A new sensitive method for qualitative and quantitative assay of neomycin phosphotransferase in crude cell extracts," *Gene* 30:211–218.

Southern, E. (1975) "Detection of specific sequences among DNA fragments separated by gel electrophoresis," *J. Mol. Biol.* 98:503–518.

Taylor, D. C., N. Weber, E.W. Underhill, M.K. Pomeroy, W.A. Keller, W.R. Scowcroft, R.W. Wilen, M.M. Moloney, and L.A. Holbrook (1990) "Storage–protein regulation and lipid accumulation in microspore embryos of *Brassica napus* L.," Planta 181: 18–26.

* cited by examiner

Primary Examiner—David T. Fox
Assistant Examiner—Francis Moonan
(74) Attorney, Agent, or Firm—Saliwanchik, Lloyd & Saliwanchik

(57) ABSTRACT

The present invention provides a novel *Brassica napus oleifera annua* variety, an agronomically superior high oleic canola variety having a unique fatty acid profile, designated "SVO95-08". Also provided in the present invention are seeds of canola variety SVO95-08, plants produced from seeds of SVO95-08, and tissue cultures of regenerable cells of the canola plant grown from SVO95-08 seed.

11 Claims, No Drawings

SPRING CANOLA (BRASSICA NAPUS) VARIETY SVO95-08

BACKGROUND OF THE INVENTION

The genus Brassica includes one of the world's most important oilseed crops, canola. Considerable effort has been made to improve its agronomic qualities by selective breeding techniques. The goals for improving this crop include increased yield and disease resistance, in addition to altering the oil content and composition.

BRIEF SUMMARY OF THE INVENTION

The present invention provides a novel *Brassica napus oleifera annua* variety, an agronomically superior high oleic canola variety having a unique fatty acid profile, designated "SVO95-08," also known as Nex-700. Also provided in the present invention are seeds of canola variety SVO95-08, plants produced from seeds of SVO95-08, and tissue cultures of regenerable cells of the canola plant grown from SVO95-08 seed.

Definitions

As used herein, the following definitions are provided:

Definitions of Classification Terms for Variety Description of Canola Cultivar SVO95-08

1.0 Classification
  1.1 Botanical and common name: The genus, species, and type define the botanical classification of the variety.
  1.2 Type of variety: The type of variety defines the method of propagation of the variety as: Open pollinated (planted in isolation and plants allowed to inter mate), Hybrid (made by crossing two or more inbred parents), Self-pollinated (plants of the variety do not inter mate, but rather are completely self-pollinating), First generation synthetic (the variety sold is the product of the first generation of all possible intercrosses between a selected set of 3 or more inbred parents), Advanced generation synthetic (the variety sold is the product of repeated inter mating generations from a first generation synthetic).
2.0 Seasonal Type
  Two seasonal variety types exist: Spring (planted in the spring to early summer, flower mid-summer and harvested in the late summer to fall) and Winter (planted in the late summer to fall, stay in a rosette form without flowering over the winter, flower late spring and harvested mid to late summer).
3.0 Characteristics of Plants Before Flowering
  3.1 Cotyledon width: The cotyledons are leaf structures that form in the developing seeds of canola and which make up the majority of the mature seed of these species. When the seed germinates, the cotyledons are pushed out of the soil by the growing hypocotyl (segment of the seedling stem below the cotyledons and above the root) and they unfold as the first photosynthetic leafs of the plant. The width of the cotyledons varies by variety and can be classified as narrow, medium, or wide.
  3.2 Seedling growth habit: The rosette consists of the first 2–8 true leaves and a variety can be characterized as having a strong rosette (closely packed leaves) or a weak rosette (loosely arranged leaves).
  3.3 Stem—intensity of anthocyanin coloration: The stems and other organs of canola plants can have varying degrees of purple coloration which is due to the presence of anthocyanin (purple) pigments. The degree of coloration is somewhat subject to growing conditions, but varieties typically show varying degrees of coloration ranging from: absent (no purple)/very weak to very strong (deep purple coloration).
  3.4 Leaf—development of lobes: The leaves on the upper portion of the stem can show varying degrees of development of lobes which are disconnected from one another along the petiole of the leaf. The degree of lobing is variety specific and can range from absent (no lobes)/weak through very strong (abundant lobes).
  3.5 Leaf—indentation of margin: The leaves on the upper portion of the stem can also show varying degrees of serration along the leaf margins. The degree of serration or indentation of the leaf margins can vary from absent (smooth margin)/weak to strong (heavy sawtooth like margin).
  3.6 Leaf—blade color: The color of the leaf blades is variety specific and can range from light to medium dark green to blue green.
  3.7 Leaf—pubescence: The leaf pubescence is the degree of hairiness of the leaf surface and is especially useful for distinguishing between the canola species. There are two main classes of pubescence which are glabrous (smooth/not hairy) and pubescent (hairy) which mainly differentiate between the *B. napus* and *B. rapa* species, respectively.
  3.8 Leaf—glaucosity: This refers to the waxiness of the leaves and is characteristic of specific varieties although environment can have some effect on the degree of waxiness. This trait can range from absent (no waxiness)/weak through very strong. The degree of waxiness can be best determined by rubbing the leaf surface and noting the degree of wax present.
  3.9 Leaf—attachment to the stem: This trait is especially useful for distinguishing between the two canola species. The base of the leaf blade of the upper stem leaves of *B. rapa* completely clasp the stem whereas those of the *B. napus* only partially clasp the stem. Those of the mustard species do not clasp the stem at all.
  3.10 Leaf—surface: The leaf surface can also be used to distinguish between varieties. The surface can be smooth or rugose (lumpy) with varying degrees between the two extremes.
4.0 Characteristics of Plants After Flowering
  4.1 Flowering date: This is measured by the number of days from planting to the stage when 50% of the plants in a population have one or more open flowers. This varies from variety to variety.
  4.2 Plant height: This is the height of the plant at the end of flowering if the floral branches are extended upright (i.e., not lodged). This varies from variety to variety and although it can be influenced by environment, relative comparisons between varieties grown side by side are useful for variety identification.
  4.3 Growth habit: At the end of flowering, the angle relative to the ground surface of the outermost fully expanded leaf petioles is a variety specific trait. This trait can range from erect (very upright along the stem) to prostrate (almost horizontal and parallel with the ground surface).
  4.4 Flower buds—location: The location of the unopened flower buds relative to the adjacent opened flowers is useful in distinguishing between the canola species.

The unopened buds are held above the most recently opened flowers in *B. napus* and they are positioned below the most recently opened flower buds in *B. rapa*.

4.5 Petal color: The petal color on the first day a flower opens can be a distinguishing characteristic for a variety. It can be white, varying shades of yellow or orange.

4.6 Anther dotting: The presence/absence of anther dotting (colored spots on the tips of anthers) and if present, the percentage of anther dotting on the tips of anthers in newly opened flowers is also a distinguishing trait for varieties.

4.7 Anther arrangement: The orientation of the anthers in fully opened flowers can also be useful as an identifying trait. This can range from introse (facing inward toward pistil), erect (neither inward nor outward), or extrose (facing outward away from pistil).

4.8 Anther fertility: This is a measure of the amount of pollen produced on the anthers of a flower. It can range from sterile (such as in female parents used for hybrid seed production) to fertile (all anthers shedding).

4.9 Silique (pod)—type: This is typically a bilateral single pod for both species of canola and is not really useful for variety identification within these species.

4.10 Silique (pod)—length: This is the length of the fully developed pods and can range from short to medium to long. It is best used by making comparisons relative to reference varieties.

4.11 Silique (pod)—width: This is the width of the fully developed pods and can range from narrow to medium to wide. It is best used by making comparisons relative to reference varieties.

4.12 Silique (pod)—habit: This is also a trait which is variety specific and is a measure of the orientation of the pods along the racemes (flowering stems). This trait can range from erect (pods angled close to racemes) through horizontal (pods perpendicular to racemes) through arching (pods show distinct arching habit).

4.13 Silique (pod)—length of beak: The beak is the segment at the end of the pod which does not contain seed (it is a remnant of the stigma and style for the flower). The length of the beak can be variety specific and can range form short through medium through long.

4.14 Silique (pod)—length of pedicel: The pedicel is the stem that attaches the pod to the raceme of flowering shoot. The length of the pedicel can be variety specific and can vary from short through medium through long.

4.15 Maturity: The maturity of a variety is measured as the number of days between planting and physiological maturity. This is useful trait in distinguishing varieties relative to one another.

5.0 Seed Characteristics 5.1 Seed coat—color: The color of the seed coat can be variety specific and can range from black through brown through yellow. Color can also be mixed for some varieties.

5.2 Seed coat—mucilage: This is useful for differentiating between the two species of canola with *B. rapa* varieties having mucilage present in their seed coats whereas *B. napus* varieties do not have this present. It is detected by imbibing seeds with water and monitoring the mucilage that is exuded by the seed.

6.0 Agronomic Characteristics 6.1 Resistance to lodging: This measures the ability of a variety to stand up in the field under high yield conditions and severe environmental factors. A variety can have good (remain upright), fair, or poor (falls over) resistance to lodging. The degree of resistance to lodging is not expressed under all conditions but is most meaningful when there is some degree of lodging in a field trial.

7.0 Reaction to Diseases

The reaction of varieties to various diseases which affect canola can also be useful in differentiating varieties. The two main diseases rated in canola are blackleg (causes lesions in the lower stems which cut off water and nutrient flow in the stem) and white rust (only a problem in the *B. rapa* species).

8.0 Quality Characteristics 8.1 Oil content: This is measured as percent of the whole dried seed and is characteristic of different varieties. It can be determined using various analytical techniques such as NMR, NIR, and Soxhlet extraction.

8.2 Percentage of total fatty acids: This is determined by extracting a sample of oil from seed, producing the methyl esters of fatty acids present in that oil sample and analyzing the proportions of the various fatty acid in the sample using gas chromatography. The fatty acid composition can also be a distinguishing characteristic of a variety.

8.3 Maximum amount of erucic acid allowed in foundation seed of this variety for pedigreed seed purity determination. The level of erucic acid in foundation seed lots is determined to arrive at this figure which is useful for purity determinations.

8.4 Protein content: This is measured as percent of whole dried seed and is characteristic of different varieties. This can be determined using various analytical techniques such as NIR and Kjeldahl.

8.5 Glucosinolates: These are measured in micromoles ($\mu$m) of total alipathic glucosinolates per gram of air-dried oil-free meal. The level of glucosinolates is somewhat influenced by the sulfur fertility of the soil, but is also controlled by the genetic makeup of each variety and thus can be useful in characterizing varieties.

DETAILED DISCLOSURE OF THE INVENTION

Spring canola variety SVO95-08 ("SVO95-08") is an agronomically superior, high oleic and low linoleic acid canola variety (*Brassica napus oleifera annua*) developed at the Agrigenetics Madison laboratories by microspore culture from the cross Cyclone (canola) X AG021 (high oleic canola).

Development of the Invention: H080-01, a high (75%) oleic mutant of the canola variety Regent, was developed by SunGene Technologies using chemical mutagenesis (U.S. patent application Ser. No. 518,669, now abandoned). The high oleic gene from this mutant was crossed with the low linolenic acid gene from the germplasm accession BN0010 in the greenhouse at the Agrigenetics Madison, Wis. laboratories. From this cross an F3 single plant selection was identified, 90W114-04-12-88, with 80.5% oleic acid and 1.3% linolenic acid. 90W114-04-12-88 was crossed as male parent onto the spring Canola variety Global (cross designation 91S070). An F3 half-seed selection from this cross, 91S0070-18-117-143, was identified with 80.1 % oleic acid and 1.8% linolenic acid. The plant arising from this F3 half-seed was crossed as male to the spring canola variety Global (BC1 to Global, cross designation 93S090). An F2 half-seed selection from this cross, 93S090-5-402, was identified with 77.3% oleic acid and 2.2% linolenic acid.

This single F2 plant selection was increased and the bulk F3 was tested as the high oleic acid/low linolenic acid strain SVO95-08. SVO95-08 was evaluated in field trials beginning in 1995. SVO95-08 was subsequently registered for contract production in Canada and is being used for commercial production of high oleic acid/low linolenic acid Canola oil under the variety name Nex-700.

The subject novel canola variety can be genetically engineered to include a selected gene (gene of interest) using known transformation methods routine in the art such that expression of the gene of interest is observed. Methods of transformation include use of Agrobacterium, viral vectors, microinjection, PEG, biolistics, and electroporation which are all routinely used to introduce foreign DNA into plant cells. Once in the cell, the foreign DNA incorporates into the plant genome. In a preferred embodiment, the transformation contemplates constructing a vector comprising plant regulatory sequences and a gene(s) of interest, placing the vector into a selected strain of Agrobacterium, and infecting selected plant cells with the Agrobacterium under conditions sufficient to result in transfer of at least some of the vectors from the Agrobacterium to the plant cells, whereby the gene of interest is expressed in the plant cells. Regulatory sequences can include both promoter and termination sequences.

Possible regulatory sequences include, but are not limited to, any promoter already shown to be constitutive for expression, such as those of viral origin (CaMV 19S and 35S, TMV, AMV) or so-called "housekeeping" genes (ubiquitin, actin, tubulin) with their corresponding termination/poly A+sequences. Also, seed-and/or developmentally-specific promoters, such as those from plant fatty acid/lipid biosynthesis genes (ACPs, acyltransferases, desaturases, lipid transfer protein genes) or from storage protein genes (zein, napin, cruciferin, conglycinin, or lectin genes, for example), with their corresponding termination/poly A+sequences can be used for targeted expression. In addition, the gene can be placed under the regulation of inducible promoters and their termination sequences so that gene expression is induced by light (rbcS-3A, cab-1), heat (hsp gene promoters) or wounding (mannopine, HGPGs). It is clear to one skilled in the art that a promoter may be used either in native or truncated form, and may be paired with its own or a heterologous termination/polyA+sequence, and enhancers as are known in the art.

In addition, expressed gene products may be localized to specific organelles in the plant cell by ligating DNA coded for peptide leader sequences to the gene of interest. Such leader sequences can be obtained from several genes of either plant or other sources. These genes encode cytoplasmically-synthesized proteins directed to, for example, mitochondria (the F1-ATPase beta subunit from yeast or tobacco, cytochrome c1 from yeast), chloroplasts (cytochrome oxidase subunit Va from yeast, small subunit of rubisco from pea), endoplasmic reticulum lumen (protein disulfide isomerase), vacuole (carboxypeptidase Y and proteinase A from yeast, phytohemagglutinin from French bean), peroxisomes (D-aminoacid oxidase, uricase) and lysosomes (hydrolases).

A selectable marker gene for optimum transformation selection is preferably employed. Such markers are typically genes which encode resistance to various toxic chemicals such as antibiotics and herbicides; the resistance is usually conferred by enzymes which typically render the chemical non-toxic to the transgenic plant. Such toxic chemicals include, for example, hygromycin, kanamycin, methotrexate, phosphinothricin, glyphosate, and bromoxynil. Enzymes which confer resistance to these chemicals are hygromycin phosphotransferase, neomycin phosphotransferase, dihydrofolate reductase, phosphinthricin acetyl transferase, ESPS, and AHAS. Genes which code for resistance are well known to those of ordinary skill in the art of plant transformation. Plants transformed with such genes are able to grow in the presence of the toxic compound, while non-transformed plants are not. Therefore, such genes serve both as a means of selecting transformed plants and as a marker for transformation, indicating that transformation has occurred.

Plant tissue useful in accord with the teachings herein includes, but is not limited to, leaves, hypocotyls, cotyledons, stems, callus, single cells that contain a biological control agent gene, and protoplasts.

In a particular embodiment, transformed callus tissue is selected by growth on selection medium (e.g., medium which contains a toxic chemical and for which the transformed plant contains a resistance gene, by virtue of its transformation). Transformed plants are regenerated and screened for the presence of the expressed gene product. This involves analyzing tissue by at least one molecular or biological assays to determine which, if any, transformants contained the biocontrol agent polynucleotides or proteins. These assays include assays of the tissue for the expression of the resistance gene enzyme, and assays of the tissue for the presence of control agent polynucleotide by, for example, a Southern assay or a PCR assay.

Those plants which are positive for the gene of interest are grown to maturity, and tissue can be analyzed for expression of the gene of interest by looking for the polypeptide encoded by the polynucleotide, as for example via a Western blot analysis.

It is now well known in the art that when synthesizing a gene for improved expression in a host cell it is desirable to design the gene such that its frequency of codon usage approaches the frequency of codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a plant cell can be calculated by averaging frequency of preferred codon usage in a large number of genes expressed by the plant cell. It is preferable that this analysis be limited to genes that are highly expressed by the host cell. Alternatively, the gene may be synthesized to have a greater number of the host's most preferred codon for each amino acid, or to reduce the number of codons that are rarely used by the host.

Thus, in one embodiment of the subject invention, plant cells can be genetically engineered, e.g., transformed with genes to attain desired expression levels. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for said plant cell, and to eliminate sequences that cause destabilization, inappropriate polyadenylation, degradation and termination of RNA, and to avoid sequences that constitute secondary structure hairpins and RNA splice sites. For example, in synthetic genes, the codons used to specify a given amino acid can be selected with regard to the distribution frequency of codon usage employed in highly expressed genes in the plant cell to specify that amino acid. As is appreciated by those skilled in the art, the distribution frequency of codon usage utilized in the synthetic gene is a determinant of the level of expression.

EXAMPLES

The key characteristics and traits of the SVO95-08 variety are presented in the data of Table 1. This table presents extensive morphological and physiological differences between the SVO95-08 variety and check varieties R1 (LEGEND), R2, (A.C. EXCEL), R3 (CYCLONE), and R4 (APOLLO). The objective description of SVO95-08 is provided in Table 1.

TABLE 1

Objective Description of Variety SVO95-08.

| | | | | | | |
|---|---|---|---|---|---|---|
| 1.0 CLASSIFICATION | | | | | | |
| 1.1 Botanical and common name (check one): | | | | | | |
| Genus | Species | Type | | | | |
| Brassica | napus L. | Canola | | | | |
| 1.2 Type of variety | 1-open pollinated | | | | | |
| 2.0 SEASONAL TYPE (#) | | CV | R1 | R2 | R3 | R4 |
| spring | 1 | 1 | 1 | 1 | 1 | 1 |
| winter | 2 | | | | | |
| other (specify) | 3 | | | | | |
| 3.0 CHARACTERISTICS OF PLANTS BEFORE FLOWERING | | | | | | |
| 3.1 Cotyledon width | | | | | | |
| narrow | 3 | 6 | 5 | 5 | 5 | 5 |
| medium | 5 | | | | | |
| wide | 7 | | | | | |
| 3.2 Seedling growth habit (leaf rosette) | | | | | | |
| weak rosette | 1 | 5 | 5 | 5 | 5 | 5 |
| strong rosette | 9 | | | | | |
| 3.3 Stem: intensity of anthocyanin colouration (#) | | | | | | |
| absent or very weak | 1 | 1 | 1 | 1 | 1 | 1 |
| weak | 3 | | | | | |
| medium | 5 | | | | | |
| strong | 7 | | | | | |
| very strong | 9 | | | | | |
| 3.4 Leaf: development of lobes (observe fully developed upper stem leaves) (#) | | | | | | |
| absent or very weak | 1 | 4 | 3 | 3 | 7 | 4 |
| weak | 3 | | | | | |
| medium | 5 | | | | | |
| strong | 7 | | | | | |
| very strong | 9 | | | | | |
| 3.5 Leaf: indentation of margin (observe fully developed upper stem leaves) (#) | | | | | | |
| absent or very weak | 1 | 3 | 3 | 3 | 5 | 3 |
| weak | 3 | | | | | |
| medium | 5 | | | | | |
| strong | 7 | | | | | |
| very strong | 9 | | | | | |
| 3.6 Leaf: blade colour (observe at 5-leaf stage) | | | | | | |
| light green | 1 | 2 | 2 | 2 | 2 | 2 |
| medium green | 2 | | | | | |
| dark green | 3 | | | | | |
| blue green | 4 | | | | | |
| 3.7 Leaf: pubescence | | | | | | |
| glabrous | 1 | 1 | 1 | 1 | 1 | 1 |
| pubescent | 9 | | | | | |
| 3.8 Leaf: glaucosity | | | | | | |
| absent or very weak | 1 | 5 | 5 | 5 | 5 | 5 |
| weak | 3 | | | | | |
| medium | 5 | | | | | |
| strong | 7 | | | | | |
| very strong | 9 | | | | | |
| 3.9 Leaf: attachment to stem (+) | | | | | | |
| complete clasping | 1 | 2 | 2 | 2 | 3 | 2 |
| partial clasping | 2 | | | | | |
| non-clasping | 3 | | | | | |
| 3.10 Leaf: surface | | | | | | |
| smooth | 1 | 4 | 3 | 3 | 2 | 3 |
| rugose | 9 | | | | | |
| 4.0 CHARACTERISTICS OF PLANTS AFTER FLOWERING | | | | | | |
| 4.1 Flowering date (number of days from planting to 50% of plants showing one or more open flowers) (#) | | | | | | |
| days to flowering | | 53 | 50 | 51 | 50 | 51 |
| 4.2 Plant height (at end of flowering) (#) | | | | | | |
| short | 1 | 7 | 5 | 7 | 6 | 6 |
| medium | 5 | | | | | |
| tall | 9 | | | | | |
| 4.3 Growth habit (at end of flowering - angle of outermost fully expanded leaf petioles with soil surface) | | | | | | |
| erect (>85°) | 1 | 3 | 4 | 5 | 4 | 3 |
| open (approx. 65°) | 3 | | | | | |
| semi-prostrate (approx. 45°) | 5 | | | | | |
| prostrate (<30°) | 7 | | | | | |
| 4.4 Flower buds: location (+) | | | | | | |
| buds above most recently opened flowers | 1 | 1 | 1 | 1 | 1 | 1 |
| buds below most recently opened flowers | 2 | | | | | |
| 4.5 Petal colour (observe on first day of flowering) (#) | | | | | | |
| white | 1 | 2–3 | 3 | 3 | 3 | 3 |
| light yellow | 2 | | | | | |
| medium yellow | 3 | | | | | |
| dark yellow | 4 | | | | | |
| orange | 5 | | | | | |
| other (specify) | 6 | | | | | |
| 4.6 Anther dotting (percentage at opening of flower) | | | | | | |
| absent | 1 | 1 | 1 | 1 | 1 | 1 |
| present | 2 | | | | | |
| (state percentage) | | | | | | |
| 4.7 Anther arrangement (observe fully opened flower) | | | | | | |
| introse (facing inward) | 1 | 3 | 3 | 3 | 3 | 3 |
| erect | 2 | | | | | |
| extrose (facing outward) | 3 | | | | | |
| 4.8 Anther fertility (measured by pollen production) | | | | | | |
| sterile | 1 | 9 | 9 | 9 | 9 | 9 |
| all anthers shedding | 9 | | | | | |
| 4.9 Silique (pod): type | | | | | | |
| bilateral single | 1 | 1 | 1 | 1 | 1 | 1 |
| other (specify) | 2 | | | | | |

TABLE 1-continued

Objective Description of Variety SVO95-08.

| 4.10 Silique (pod): length (#) | | | | | | |
|---|---|---|---|---|---|---|
| short | 3 | 5 | 5 | 4 | 5 | 5 |
| medium | 5 | | | | | |
| long | 7 | | | | | |
| 4.11 Silique (pod): width (#) | | | | | | |
| narrow | 3 | 5 | 5 | 5 | 4 | 4 |
| medium | 5 | | | | | |
| wide | 7 | | | | | |
| 4.12 Silique (pod): habit (#) | | | | | | |
| erect | 1 | 4 | 4 | 4 | 4 | 4 |
| semi-erect | 3 | | | | | |
| horizontal | 5 | | | | | |
| semi-arching | 7 | | | | | |
| arching | 9 | | | | | |
| 4.13 Silique (pod): length of beak | | | | | | |
| short | 3 | 5 | 5 | 5 | 4 | 5 |
| medium | 5 | | | | | |
| long | 7 | | | | | |
| 4.14 Silique (pod): length of pedicel | | | | | | |
| short | 3 | 4 | 5 | 5 | 5 | 5 |
| medium | 5 | | | | | |
| long | 7 | | | | | |
| 4.15 Maturity (number of days from planting to maturity) | | | | | | |
| days to maturity | | 101 | 98 | 98 | 97 | 98 |
| 5.0 SEED CHARACTERISTICS | | | | | | |
| 5.1 Seed coat: colour (#) | | | | | | |
| black | 1 | 1 | 1 | 1 | 1 | 1 |
| brown | 2 | | | | | |
| yellow | 3 | | | | | |
| mixed (describe) | 4 | | | | | |
| other (describe) | 5 | | | | | |
| 5.2 Seed coat: mucilage (+) | | | | | | |
| absent | 1 | 1 | 1 | 1 | 1 | 1 |
| present | 9 | | | | | |
| 6.0 AGRONOMIC CHARACTERISTICS | | | | | | |
| 6.1 Resistance to lodging (#) | | | | | | |
| not tested | 0 | 7 | 5 | 6 | 6 | 4 |
| poor | 3 | | | | | |
| fair | 5 | | | | | |
| good | 7 | | | | | |
| 7.0 REACTION TO DISEASES | | | | | | |
| 0 - Not tested | | 5 - Moderately susceptible | | | | |
| 1 - Resistant | | 7 - Susceptible | | | | |
| 3 - Moderately resistant | | 9 - Highly susceptible | | | | |
| 7.1 Blackleg: Leptosphaeria maculans Asexual stage: Phoma lingam | | 3 | 5 | 5 | 3 | 7 |
| 7.2 White rust, Staghead: Albugo candida Specify races: RACE 2V RACE 7V | | 1 | 1 | 1 | 1 | 1 |
| 8.0 QUALITY CHARACTERISTICS | | | | | | |
| 8.1 Oil content (percentage in whole dried seed) (#) | | | | | | |
| percentage | | 44 | 45 | 46 | 44 | 45 |
| 8.2 Percentage of total fatty acids (express as a percentage (%) of the oil) Confidential Business Information | | | | | | |
| 8.2.1 erucic (22:1) | | 0.1 | N.D. | 0.6 | N.D. | 0.1 |
| 8.2.2 palmitic (16:0) | | 3.5 | 3.8 | 3.8 | 3.9 | 3.8 |
| 8.2.3 stearic (18:0) | | 2.0 | 7.2 | 2.1 | 1.8 | 2.3 |
| 8.2.4 oleic (18:1) | | 74.0 | 65.0 | 65.6 | 64.1 | 67.8 |
| 8.2.5 linoleic (18:2) | | 14.4 | 18.7 | 17.2 | 18.8 | 21.3 |
| 8.2.6 linolenic (18:3) | | 7.5 | 7.2 | 8.5 | 1.9 | 2.2 |
| 8.3 Maximum amount of erucic acid allowed in foundation seed of this variety for pedigreed seed (#) purity determination (% of total fatty acids) 0.8% | | | | | | |
| 8.4 Protein content (percentage in whole dried seed) (#) | | | | | | |
| percentage | | 49 | 51 | 51 | 50 | 49 |
| 8.5 Glucosinolates (μ moles - total aliphatic glucosinolates per gram air dried oil free meal) | | | | | | |
| very low (<10 μmol per gram) | 1 | 2 | 2 | 3 | 1 | 1 |
| low (10–15 μmol per gram) | 2 | | | | | |
| medium (15–20 μmol per gram) | 3 | | | | | |
| high (>20 μmol per gram) | 4 | | | | | |

Legend:
R1 = Legend
R2 = AC Excel
R3 = Cyclone
R4 = Apollo

As can be seen from the information in Table 1, those characteristics which are most useful in distinguishing variety SVO95-08, also known as Nex-700, from other canola varieties are listed in key numbers 3.1; 3.4; 3.5; 3.10; 4.1; 4.2; 4.15; 6.1; and 8.2.

Deposits

Applicant has made available to the public without restriction a deposit of at least 2500 seeds of the SVO95-08 variety with the American Type Culture Collection (ATCC), Rockville, Md. 20852. The deposit has been designated as ATCC Deposit No. PTA-2086. The deposit will be maintained without restriction at the ATCC depository, which is a public depository, for a period of 30 years, or five years after the most recent request, or for the effective life of the patent, whichever is longer, and will be replaced if it becomes nonviable during that period.

The following examples represent routine protocols for transformation and tissue culture techniques for use with *Brassica napus*. While the varieties utilized in the following examples are different from the subject variety, the protocols taught therein are intended to be general in nature and can broadly be applied. Accordingly, the subject novel variety SVO95-08 can be successfully substituted for any of the cultivars specified below.

Genetic Transformation of *Brassica napus*

Plant Materials. The cultivars used in this study included *B. napus* cv. Westar and Profit and *B. rapa* cv. Parkland. As noted above, these can be substituted by the novel canola variety "SVO95-08." Seeds were surface sterilized with 1.05% sodium hypochlorite for 20 minutes and rinsed 3 times with sterile distilled water. These seeds were aseptically germinated on basal medium (BM) in 20×100 mm petri dishes for 4–6 days. The BM consisted of Murashige and Skoog (1962) macro- and micro-elements, iron as 40 mg/l FeNa2EDTA, and the following constituents (mg/l): myo-inositol 100; nicotinic acid 0.1; pyridoxine HCl 0.1; thiamine HCl 0.02; glycine 0.4; sucrose 30,000; Difco bacto agar 8,000. The seedlings were grown at 25° C. with a photoperiod of 16 hours. Hypocotyl segments (2–3 mm)

were excised from 4–6 days old seedlings and pre-treated for 24 hours on BM or Gamborg's B5 (Gamborg et al. 1968) medium containing α-naphthaleneacetic acid (NAA) at 5 mg/l or 2,4-dichlorophenoxy acetic acid (2,4-D) at 1 mg/l (callusing medium) depending on the cultivar used. A sterile filter paper was placed on the medium prior to treatment.

Cotyledon explants were excised from 6 day old seedlings ensuring that 2–3 mm of the petioles were left intact with the lamina. These explants were pre-treated for 1 day on BM containing 6-benzylaminopurine (BAP) at 4 mg/l. The cotyledonary petioles were then embedded in the medium.

Vectors. The vectors used in these experiments were pH602 or pH610 in the *Agrobacterium tumefaciens* strain 2707S, which is a disarmed C58 derivative. Both vectors contain the hygromycin phosphotransferase (HPT) gene that confers resistance to the antibiotic hygromycin. The plasmid pH602 contains the HPT gene driven by the CaMV 35S promoter. The second plasmid pH610, which is a derivative of pH602, also contains a truncated *Bacillus thuringiensis* toxin gene driven by the mannopine promoter (Adang et al. 1987).

Transformation Procedure. The hypocotyl segments and the cotyledon explants were treated with the Agrobacterium solution (diluted to $10^8$/ml with liquid basal medium) for 30 min. and then placed onto the callusing medium for 2–3 days of co-cultivation. The hypocotyl tissues were transferred to the callusing medium containing 500 mg/l carbenicillin and 5–10 mg/l hygromycin. The cultures were maintained at 22±2° C. with 16 hrs photoperiod. After 7 days, the hypocotyl segments were transferred to shoot regeneration medium BM or B5 containing 1–4 mg/l BAP, 0–4 mg/l zeatin, 2.5–10 mg/l silver nitrate (AgNO3), 500 mg/l carbenicillin and 5–10 mg/l hygromycin; the concentrations were dependent on the cultivar and the vector being used. The callusing and regeneration media were solidified with 0.5% Agarose (SeaKem) or 0.2% Gelrite. The tissues were transferred to fresh selection medium every 3 weeks. Callusing occurred after 1–3 weeks and shoots were formed after 3–6 weeks. These shoots were then transferred to BM containing 0.01–0.1 mg/l BAP and carbenicillin for elongation and later were rooted on BM with 0.1 mg/l indole butyric acid (IBA).

After treatment with Agrobacterium, cotyledon explants were transferred to selection medium containing BAP (4 mg/l), carbenicillin and hygromycin at the same levels used for hypocotyls. Shoots formed on the cotyledonary petiole were visible within 3–6 weeks and were cultured using the same protocol as for hypocotyls.

Molecular and Biological Assays. All plants were assayed and determined to be transgenic by the following molecular and biological assays:

Polymerase Chain Reaction—A linked reverse transcription and PCR assay modified from Frohman et al. (1988) was used to analyze small amounts of leaf tissue for the presence of RNA transcripts from the HPT gene.

Hygromycin Phosphotransferase (HPT) Activity—a rapid dot-blot assay based on the methods of Reiss et al. (1984) developed for antibiotic phosphotransferases was used to assay HPT activity.

Leaf Disc Assay—Small leaf sections (2–3 mm square) isolated from shoots obtained on selection medium were cultured on BM containing 4 mg/l BAP, 0.5 mg/l NAA and 10 mg/l hygromycin for 4 weeks.

Southern Analysis—The presence of the HPT gene in plant DNA was determined by Southern analysis (Southern, 1975) using an internal DNA segment from the structural gene as a probe.

Genetic Analysis. Transgenic (Ro) plants were self-pollinated and the R1 seeds were surface sterilized and germinated on BM containing 20 mg/l hygromycin for identifying those seedlings that expressed the HPT gene. Resistance or sensitivity of the seedlings was scored after 3 weeks.

Transformation. The response of several different tissue types including hypocotyl segments, longitudinal stem segments and cotyledonary petioles to Agrobacterium-mediated transformation was compared. All explant sources yielded transgenic plants.

We have selected hypocotyl segments as the preferred donor tissue because we can consistently regenerate transgenic plants. It further offers the advantage that large amounts of donor material are available within 4–5 days of seed germination. After co-cultivation of the hypocotyls with Agrobacterium, the resultant calli were transformed at a high frequency (70–80%). These calli gave rise to transgenic shoots at a frequency of up to 13%. Of the shoots regenerated from calli on the selection medium, more than 90% were transgenic. Once week treatment on callusing selection medium (2,4-D or NAA) and then transfer to the regeneration medium was essential for obtaining a high transformation frequency. Formation of transgenic shoots was significantly reduced by culture of hypocotyl tissues on a hormone combination that promoted both callusing and regeneration.

A higher frequency (40–60%) of shoot regeneration was obtained by incorporating AgNO3 (2.5–10 mg/l) in the culture medium as compared to the frequency (10–15%) obtained on medium lacking AgNO3. Timing of AgNO3 incorporation was equally important, being more effective when incorporated only in the regeneration medium and not in the callusing medium.

The use of hygromycin provided a very "tight" selection system and significantly reduced the possibility of any "escapes." Over 90% of the plants that came through the selection procedure were transgenic. Direct selection, i.e., culturing hypocotyl segments on hygromycin medium directly after co-cultivation was essential for obtaining primarily transgenic plants. Delayed selection by culturing the tissues on non-selective medium for 3–7 days before transfer to selection medium allowed more "escapes" to form. We have regenerated more than 200 transgenic plants using this procedure and these plants show normal morphological characteristics.

This procedure has been used to successfully transform 3 different cultivars of 2 species of Brassica.

Expression and Integration. Transformation was confirmed by the molecular assays (PCR assay, Hygromycin phosphotransferase activity assay and Southern analysis) and the biological assay (Leaf disc assay). Over 90% of the shoots which regenerated under hygromycin selection were transformed as determined by these analyses performed on leaf samples. See following schematic.

Transformation Procedure

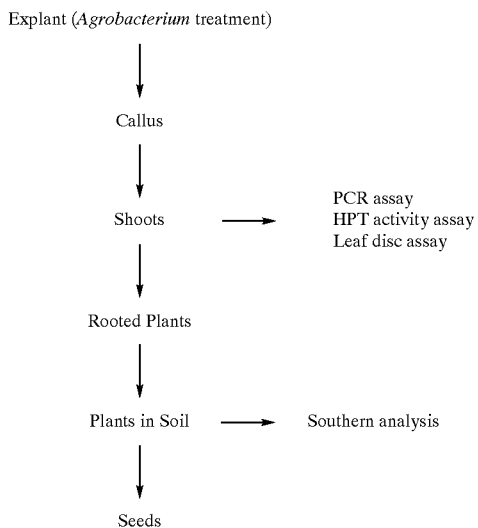

The PCR assay was performed on RNA isolated from a small amount of leaf tissue. The primer sequences yield a 600 bp DNA fragment when the RNA transcripts of the HPT gene are present.

The level of HPT activity was determined by the dot blot assay. As shown in FIG. 3 there were varying levels of HPT activity in the transgenic plants.

For the leaf disc assay, callusing of the leaf tissues on hygromycin containing medium was determined after 4 weeks. Explants from transgenic shoots expanded and formed a dark green callus which regenerated roots and/or shoots. Tissues from non-transgenic control plants turned white or brown and showed no expansion.

The above assays are very useful for early detection of transgenic plants because these require only 50–100 mg of leaf tissue. Results from leaf disc assays and Southern analyses correlated 100%; all the shoots determined positive with leaf disc assay were positive with Southern blots. Results from the expression assays (PCR and HPT activity) correlated 80–90% with PCR and HPT activity assays were positive by Southern blots.

Southern hybridizations of the DNA from thirty-two plants confirmed the insertion of T-DNA in each transgenic plant; all DNA samples hybridized to the probe for the HPT gene. Plants regenerated from the same callus had an identical pattern of restriction fragments, indicating they arose from the same transformation event.

Genetic Analysis. Genetic inheritance of the HPT gene was determined by scoring the progeny of he transgenic plants for tolerance to hygromycin. Seeds (R1) from five independent transgenic plants were analyzed for inheritance of T-DNA by growing seeds from these plants on selection medium containing hygromycin. Inheritance data shows that the hygromycin resistance marker segregates as one or two Mendelian loci.

Tissue Culture of *Brassica napus*

Donor Plants. The canola (*Brassica napus* L.) gentoypes used for the fatty acid accumulation study were the cultivars Profit, a canola type; BNO 300, a proprietary high oleic mutant out of Regent; and a high erucic type, an F3 selection 89M003-5-66. The cultivars used for the maturation and germination study were the canola types Profit, Topas, and H51, a highly embryogenic line out of Altex. Donor plants for microspore culture were grown at 10°/5° C. day/night with a 16 hour day under cool white fluorescent light at 150 $\mu$E s$^{-1}$ m$^{-2}$. The above cultivars can be substituted by the novel canola variety SVO95-08.

Microspore Culture. The culture method used was similar to Chuong and Beversdof (1985) with the following changes: the microspores were plated at a density of 60,000 cells/ml in NLN medium (Nitsch and Nitsch 1967) as modified by Lichter (1981) but without potato extract or growth hormones. Cultures were incubated in the dark at 32° C. for three days followed by 18 days of culture at 25° C. After the initial 21 day culture period, the cultures were transferred to various liquid media, shaken at 60 rpm, and cultured in no or low light (15 $\mu$E s$^{-1}$ m$^{-2}$, 16 h day), to study aspects of embryo maturation. After maturation, the embryos were germinated on solid B5 medium (Gamborg et al. 1968) in bright fluorescent light (70–100 $\mu$E s$^{-1}$ m$^{-2}$; 16 h day).

Embryo Maturation Studies. At 21 days afer culture (DAC) the embryos were at various stages of development but most were at the late torpedo to cotyledonary stage, with the largest being about 5 mm in length; The embryos were then moved to differing medium sequences, to study media effects on subsequent embryo development and germination. To transfer, the old medium was removed and fresh medium was added to the same plate. The maturation factors that were studied involved the presence or absence of three conditions: 1) an embryo enlargement phase; 2) an abcisic acid (ABA) phase; and 3) an embryo dessication phase. The enlargement phase involved transferring the embryos to NLN, B5W (B5 with 13% sucrose), or B5L (B5 with 2% sucrose) liquid media for 7–11 days. The ABA phase involved transferring the embryos to BSA (liquid B5 with 13% sucrose and 15 $\mu$M ABA). After each of these phases the embryos were plated on B5 solid medium (0.8% agar) for germination. The media used are summarized in Table 2.

TABLE 2

Media used in various maturation experiments.
Maturation Phases

| Initiation | Enlargement | ABA | Desiccation | Germination |
|---|---|---|---|---|
| NLN | NLN<br>B5L<br>B5W<br>None | NLNA<br>B5A<br>None | 1 week<br>none | B5 |

The cotyledonary stage embryos were dried by removing the remaining medium and putting the unwrapped Petri plates into a laminar flow hood for one week. The desiccated or non-desiccated embryos were scored for viability and germinability. Viability was defined as the ability of the embryos to turn green and grow roots on B5 medium. Germinability was defined as the ability of viable embryos to grow a shoot from the apex. In some cases embryo length was measured before germination and related to germinability.

Fatty Acid Accumulation Study. Samples of the microspore cultures were taken after 21 days on NLN in the dark followed by 21 days on B5A in the light and analyzed using gas chromatography (GC). For the cultures 42 DAC five embryos of normal appearance 4–7 mm in length were sampled and analyzed in bulk. Fatty acid composition was determined using GC analysis of methyl esterified total lipid extracts by the method of Christie (1982). Each extracted sample was analyzed twice. Seeds of each parental type were also analyzed.

Results

Embryo Germination. Table 3 shows the results of the varius medium sequences on germination of embryos of the genotype H51. The highest rate of germination was 90.3% where the embryos, after 21 days in the induction medium NLN, were transferred to B5W for 10 days, then to B5A for 10 days before being germinated. The addition of an enlarging step alone was beneficial with B5W and NLN superior to B5L (26.7% and 25.0% germination vs. 11.1% germination, Table 3). The embryos in the high-sucrose media B5W and NLN grew slowly over the culture period with most of the embryos becoming 3–10 mm long. The embryos in the low-sucrose B5L elongated up to 20–24 mm in length. Transferring directly to the ABA-containing medium NLNA (43.3%) germination) was an improvement over no maturation steps at all or the enlarging step alone.

TABLE 3

The effects of various maturation medium sequences on embryo germination, genotype H51.

| Enlargement Medium | ABA Medium | Dry Stage | No. Germ. | No. Total | % Germ | % Viable |
|---|---|---|---|---|---|---|
| B5L | | | 5 | 45 | 11.1 | 100.0 |
| B5W | | | 12 | 45 | 26.7 | 100.0 |
| NLN | | | 10 | 40 | 25.0 | 100.0 |
| | NLNA | | 87 | 201 | 43.3 | 100.0 |
| B5L | B5A | | 14 | 20 | 70.0 | 100.0 |
| B5W | B5A | | 28 | 31 | 90.3 | 100.0 |
| B5L | | DRY | 1 | 30 | 3.3 | 3.3 |
| NLN | | DRY | 1 | 60 | 1.7 | 8.0 |
| B5W | | DRY | 1 | 44 | 2.3 | 11.0 |
| B5W | B5W | DRY | 13 | 42 | 31.0 | 45.0 |

The B5L medium in any part of the sequence was usually detrimental, and resulted in lower germination rates (Table 3). This illustrated the need for maintaining high sucrose levels throughout the maturation sequence. This negative effect could be partially overcome by using B5A as the next step in the sequence.

Embryo Desiccation, Germination, and Viability. The data in Tables 3 and 4 show that desiccation tolerance is greatly enhanced when maturation medium sequences include an ABA-containing medium. The highest survival without ABA was 11% with only 2.3% germination, using B5W as an enlarging medium (Table 3). Table 4 shows no embryo viability at all for the cultivar Topas unless a BSA step is used before dessication. In a separate experiment (Table 5) cultivar Profit shows high rates of germination (85.2%) and viability (100%). Upon complete maturation, a sample was plated to B5 for germination or desiccated and then germinated. Rapid drying of the embryos over just a few days resulted in low viability, so drying had to be done gradually over a period of about a week (unpublished data). Table 5 also shows that there is a distinct improvement in germination when the smaller size class is plated. This was consistent over several experiments (unpublished data) with the most responsive embryos in the 3–7 mm range.

TABLE 4

The effects of various maturation medium sequences on viability and germination of desiccated embryos, genotype Topas.

| Enlargement Medium | ABA Medium | Dry Stage | No. Germ. | No. Total | % Germ | % Viable |
|---|---|---|---|---|---|---|
| B5L | | DRY | 0 | 30 | 0.0 | 0.0 |
| B5W | | DRY | 0 | 30 | 0.0 | 0.0 |
| NLN | | DRY | 0 | 32 | 0.0 | 0.0 |
| B5L | BSA | DRY | 0 | 32 | 0.0 | 0.0 |
| B5W | B5A | DRY | 9 | 52 | 17.3 | 33.0 |

TABLE 4-continued

The effects of various maturation medium sequences on viability and germination of desiccated embryos, genotype Topas.

| Enlargement Medium | ABA Medium | Dry Stage | No. Germ. | No. Total | % Germ | % Viable |
|---|---|---|---|---|---|---|
| NLN | B5A | DRY | 50 | 111 | 45.0 | 65.0 |
| B5L | NLNA | DRY | 11 | 33 | 33.3 | 48.0 |
| NLN | NLNA | DRY | 13 | 80 | 16.3 | 46.3 |

TABLE 5

Embryo germination and viability in two size classes of pre- and post- desiccated embryos, genotype.

| | Pre-dry germinated | | Post-dry germinated | | Post-dry viability |
|---|---|---|---|---|---|
| Size (mm) | No. | % | No. | % | % |
| 2–3 | 35/80 | 43.8 | 52/61 | 85.2 | 100.0 |
| 5–8 | 23/80 | 28.8 | 32/78 | 41.0 | 100.0 |

Fatty Acid Accumulation. The use of NLN for the initial 21 days followed by B5A for 21 more days in cultures of Profit, BN0300, and 89M003-5-66 resulted in levels of oleic (18:1), eicosenoic (20:1), and erucic (22:1) acids very much like that of seed (Table 6). For Profit and BNO300 the fatty acid levels in the matured microspore embryos were almost identical to the fatty acids levels in the parental seed. The highest accumulation of erucic acid in microspore embryos was 21.1% with the total of eicosenoic and erucic acids being 37.6% in genotype 89M003-5-66 (Table 3).

TABLE 6

Comparison of matured microspore embryo and seed oleic (18:1), eicosenoic (20:1), and erucic (22:1) acids. Standard deviation in parentheses.

| Genotype | Tissue | 18:1 | 20:1 | 22:1 |
|---|---|---|---|---|
| Profit | embryos | 70.6 (0.51) | 0.6 (0.08) | 0 (0.0) |
| | seeds | 59.9 (1.18) | trace | trace |
| BN0300 | embryos | 80.8 (0.61) | 0.7 (0.06) | 0.0 (0.0) |
| | seeds | 79.8 (0.84) | 0.8 (0.12) | 0.0 (0.0) |
| 89M003-5-66 | embryos | 33.8 (0.4) | 16.5 (0.10) | 21.1 (0.80) |
| | seeds | 16.2 (2.23) | 8.9 (0.83) | 41.9 (2.14) |

Although producing embryos from canola microspore cultures is now routine, germinating microspore embryos has been a problem in the past. Canola microspore embryos that are not matured typically germinate at a rate of less than 5% (Mathias 1989). Our lab produces microspore embryos that germinate at 5–10% without maturation. Most of the embryos develop into structure with swollen cotyledons and elongated hypocotyls with secondary embryos growing on them.

The embryo maturation system described herein results in embryos that are easy to germinate and may be desiccated for future regeneration. The quality of the plants produced from the germinated microspore embryos is excellent, similar to seed-derived plants. In B. napus microspore embryos, germination frequencies were improved up to 50% (Mathias 1989) by culturing torpedo stage embryos on high (1.5%) agar concentrations. Both of these systems involve a high osmotic or drying stage.

There is evidence that the application of high osmoticum or drying induces endogenous production of ABA in zygotic embryos grown in vitro (Finkelstein and Crouch 1987). Dessication tolerance has been induced with sucrose, heat, shock and ABA in alfalfa (Anandarajah and McKersie 1990). It is not necessary to apply exogenous ABA to the culture medium for canola microspores to accumulate fatty acid profiles similar to parental fatty acid profiles (Taylor et al. 1990). Exogenous ABA is needed to produce matured embryos that germinate at a high frequency and are able to survive dessication. The accumulation of C22:1 fatty acids in microspore embryos approaches but does not equal that of seed, even after maturing them on high sucrose and ABA for an extended time. Clearly there are other factors involved in the accumulation of C20:1 and C22:1 fatty acids besides ABA or high sucrose, although both are important in other aspects of embryo maturation. The fatty acid compositions in microspore embryos in all the genotypes studied were comparable to the parental seed.

The foregoing teachings are a simple efficient system that may be applied to in vitro studies genetic and biochemical regulation in developing embryos. Researchers may also use the system to streamline regeneration for application in plant breeding.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Adang, M. J., K. F. Idler, and T. A. Rocheleau (1987) "Structural and antigenic relationships among three insecticidal crystal proteins of *Bacillus thuringiensis* subsp. kurstaki," *Biotechnology in Invertebrate Pathology and Cell Culture*. Maramorosch, K. (ed.) Academic Press, pp. 85–99.

Anandarajah K. and B. D. McKersie (1990) "Manipulating the dessication tolerance and vigor of dry somatic embryos of *Medicago sativa* L. with sucrose, heat shock and abcisic acid," *Plant Cell Rep.* 9: 451–455.

Christie, W. W. (1982) "A simple procedure for rapid transmethylation of glycerolipids and cholesteryl esters," *J. Lipid. Res.* 23: 1072–1075.

Chuong, P. V. and W. D. Beversdorf (1985) "High frequency embryogenesis through isolated microspore culture in *Brassica napus* L. and *B. carinata* Braun," *Plant Sci.* 39: 219–226.

Finklestein, R. R. and M. L. Crouch (1987) "Hormonal and osmotic effects on developmental potential of maturing rapeseed," *Hort Sci.* 22: 797–800.

Finklestein, R. R. and C. Somerville (1989) "Abcisic acid or high osmoticum promote accumulation of long-chain fatty acids in developing embryos of *Brassica napus,*" *Plant Sci.* 61: 213–217.

Frohman, M. A. (1988) "Rapid production of full-length cDNAs from rare transcripts: Amplification using a single gene-specific oligonucleotide primer," *Proc. Natl. Acad. Sci. (USA)* 85:8998–9002.

Gamborg, O. L., R. A. Miller, and K. Ojima (1986) "Nutrient requirements of suspension cultures of soybean root cells," *Expt. Cell Res.* 50:151–158.

Kott, L. S., L. R. Erickson, and W. D. Beversdorf (1990) "The role of biotechnology in canola/rapeseed research," In: Canola and Rapeseed: Production, Nutrition and Processing Technology. F. Shahidi ed. Van Nostrand Reinhold, New York. pp. 47–78.

Lichter, R. (1981) "Another culture of *Brassica napus* in a liquid culture medium," *Z. Pflanzenphysoiol.* 103: 229–237.

Lichter, R. (1982) "Induction of Haploid plants from isolated pollen of *Brassica napus,*" *Z. Pflanzenphysiol.* 105: 427–434.

Mathias, R. (1988) "An improved in vitro culture procedure for embryoids derived from isolated microspores of rape (*Brassica napus* L.)," *Plant Breeding* 100: 320.

Murashige, T. and F. Skoog (1962) "A revised medium for rapid growth and bioassays with tobacco tissue cultures," *Physiol. Plant.* 15:473–497.

Nitsch, C. and J. P. Nitsch (1967) "The induction of flowering in vitro in stem segments of L *Plumbago indica,*" *Planta* 72: 355–370.

Reiss, B., R. Sprengel, H. Will, and H. Schaller (1984) "A new sensitive method for qualitative and quantitative assay of neomycin phosphotransferase in crude cell extracts," *Gene* 30:211–218.

Southern, E. (1975) "Detection of specific sequences among DNA fragments separated by gel electrophoresis," *J. Mol. Biol.* 98:503–518.

Taylor, D. C., N. Weber, E. W. Underhill, M. K. Pomeroy, W. A. Keller, W. R. Scowcroft, R. W. Wilen, M. M. Moloney, and L. A. Holbrook (1990) "Storage-protein regulation and lipid accumulation in microspore embryos of *Brassica napus* L.," *Planta* 181: 18–26.

I claim:

1. Seed of *Brassica napes* variety having ATCC accession No. PTA-2086.

2. A *Brassica napus* plant produced by the seed of claim 1.

3. A tissue culture of regenerable cells of the plant of claim 2.

4. A *Brassica napus* plant regenerated from the tissue culture of claim 3 capable of expressing all the morphological and physiological properties of variety SVO95-08 having ATCC number PTA-2086.

5. A *Brassica napus* plant having all the physiological and morphological characteristics of the plant of claim 2.

6. An $F_1$ hybrid *Brassica napus* plant having as one of its parents *Brassica napus* plant SVO95-08, said SVO95-08 having ATCC accession number PTA-2086.

7. *Brassica napus* seed produced by the $F_1$ hybrid *Brassica napus* plant of claim 6.

8. A tissue culture of regenerable cells of the plant of claim 6.

9. A method for producing an $F_1$ hybrid *Brassica napus* seed comprising crossing the plant of claim 2 with a different in-bred parent canola plant and harvesting the resultant $F_1$ hybrid *Brassica napus* seed.

10. The method of claim 9, wherein the in-bred *Brassica napus* plant produced from the seed designated SVO95-08, having been deposited under ATCC Accession number PTA-2086, is the female parent.

11. The method of claim 9, wherein inbred *Brassica napus* plant produced from the seed designated SVO95-08, having been deposited under ATCC Accession number PTO-2086, is the male parent.

\* \* \* \* \*

UNITED STATES PATENT AND TRADEMARK OFFICE
CERTIFICATE OF CORRECTION

PATENT NO. : 6,489,543 B1  Page 1 of 1
DATED : December 3, 2002
INVENTOR(S) : Larry Sernyk It is certified that error appears in the above-identified patent and that said Letters Patent is hereby corrected as shown below:

Column 10,
Line 14, "oil free meal)" should read -- oil free meal) (#) --.

Column 14,
Line 19, "5 mm in length; The" should read -- 5 mm in length. The --.
Line 30, "21 days on BSA" should read -- 21 days on B5A --.

Column 18,
Line 34, "Seed of *Brassica napes* variety" should read -- Seed of *Brassica napus* variety --.

Signed and Sealed this

Twentieth Day of January, 2004

JON W. DUDAS
*Acting Director of the United States Patent and Trademark Office*